US009642641B2

(12) United States Patent
Fernandez Dell'oca

(10) Patent No.: US 9,642,641 B2
(45) Date of Patent: May 9, 2017

(54) PLATE HOLDING BONE FORCEPS AND METHOD OF USE

(75) Inventor: Alberto A. Fernandez Dell'oca, Montevideo (UY)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1334 days.

(21) Appl. No.: 13/000,228

(22) PCT Filed: Jul. 29, 2009

(86) PCT No.: PCT/US2009/052115
§ 371 (c)(1),
(2), (4) Date: Dec. 20, 2010

(87) PCT Pub. No.: WO2010/014719
PCT Pub. Date: Feb. 4, 2010

(65) Prior Publication Data
US 2011/0106183 A1    May 5, 2011

Related U.S. Application Data

(60) Provisional application No. 61/084,294, filed on Jul. 29, 2008.

(51) Int. Cl.
*A61B 17/28* (2006.01)
*A61B 17/80* (2006.01)
*A61B 17/88* (2006.01)

(52) U.S. Cl.
CPC .......... *A61B 17/282* (2013.01); *A61B 17/808* (2013.01); *A61B 17/80* (2013.01); *A61B 17/8866* (2013.01)

(58) Field of Classification Search
USPC ................. 606/280, 281, 99, 101, 102, 105, 606/205–209; 81/303, 304, 307–311,
(Continued)

(56) References Cited

U.S. PATENT DOCUMENTS 550,879 A  * 12/1895 Golling et al. ............ 72/409.03
2,583,896 A    1/1952 Siebrandt
(Continued)

FOREIGN PATENT DOCUMENTS

DE     20 2005 01597      2/2007
DE     10 2007 018860     10/2007
GB         2 198 647       6/1988

*Primary Examiner* — David Bates
*Assistant Examiner* — Olivia C Chang
(74) *Attorney, Agent, or Firm* — Fay Kaplun & Marcin, LLP

(57) ABSTRACT

A device for the positioning of a bone plate against a bone comprises first and second arms pivotally connected at a first joint, distal ends of the first and second arms defining a gripping surface for gripping the bone therebetween, proximal portions of the first and second arms extending in a first plane. An extension member couples to the first and second arms at the first joint and includes a first section extending distally from the first joint parallel to the first plane and a second section extending distally from the first section angled relative to the first section so that when the first and second arms are in a desired configuration gripping the bone, the second section extends parallel to the bone. A compression mechanism couples to the second section and includes a compression member and a coupling member being movable toward and away from the second section.

8 Claims, 1 Drawing Sheet

(58) Field of Classification Search
USPC .................................................. 81/418, 419
See application file for complete search history.

(56) References Cited

U.S. PATENT DOCUMENTS

2005/0055031 A1     3/2005   Lim
2009/0299416 A1    12/2009   Hanni et al.

\* cited by examiner

PLATE HOLDING BONE FORCEPS AND METHOD OF USE

PRIORITY CLAIM

This application is a National Phase application of PCT Patent Application Serial No. PCT/US2009/052115 filed on Jul. 29, 2009 which claims priority to U.S. Provisional Application Ser. No. 61/084,294 entitled "Plate Holding Bone Forceps and Method of Use" filed on Jul. 29, 2008. The entire disclosures of the above-identified applications are expressly incorporated herein by reference.

FIELD OF THE INVENTION

The invention relates to a plate holing system to provisionally fix a bone plate to a bone. The plate holding system temporarily locks a position of the bone plate against the bone to aid in proper positioning of the bone plate, wherein the plate holding system may be locked and unlocked a plurality of times to position the bone plate without causing trauma to the bone.

BACKGROUND

Procedures for bone fixation comprise the use of bone fixation plates attached to fractured or otherwise damaged bone. Proper positioning of the bone plate relative to a fracture site is vital when performing these procedures to avoid a further fracture of the bone. One system of positioning a bone plate against a bone comprises the insertion of a bone screw through an elongated bone plate hole. The screw is loosely inserted into the bone and the bone plate is moved against the bone relative to the screw to a desired orientation. The screw is loosened and tightened within the bone repeatedly until a desired placement orientation is achieved. However, this system often does not provide a degree of lateral movement of the bone plate needed to maintain a corrective position of the bone plate since the bone plate is only movable within the confines of an elongated bone plate hole. Furthermore, the repeated screwing and unscrewing of the screw in the bone reduces a bony purchase of the screw, which may result in less than efficient holding force when the screw is finally tightened into the bone.

SUMMARY OF THE INVENTION

The present invention is directed to a device for the positioning of a bone plate against a target portion of bone, comprising first and second arms pivotally connected to one another at a first joint, a distal end of each of the first and second arms defining a gripping surface configured to grip a target portion of bone therebetween, portions of the first and second arms proximal of the first joint extending substantially in a first plane and an extension member coupled to the first and second arms at the first joint, the extension member including a first section extending distally from the first joint substantially parallel to the first plane and a second section extending distally from the first section angled relative to the first section so that when the first and second arms are in a desired configuration gripping a target portion of bone, the second section extends substantially parallel to a surface of the target portion of bone in combination with a compression mechanism coupled to the second section, the compression mechanism including a coupling member coupled between the second section of the extension member and a compression plate including a distal surface configured to engage a proximal surface of a bone plate to be coupled to the bone, the coupling member being movable relative to the second section of the extension member to move the compression plate toward and away from the second section.

DETAILED DESCRIPTION

The present invention may be further understood with reference to the following description and the appended drawings. The present invention relates to the treatment of a bone and, in particular, to a system directed to the positioning of a bone plate over fractured or otherwise damaged bone. An exemplary embodiment of the present invention describes a system and method for positioning a bone plate over a target portion of a fractured bone by clamping a bone forceps to a target region of a bone adjacent to a fracture line and manipulating a bone plate holding element attached to the bone forceps to apply a compressive force holding the bone plate against the bone. Although exemplary embodiments of the present invention specifically describe a fixation of a fracture of the radius, it will be understood by those of skill in the art that the present invention may be used to treat a fracture of a variety of bones. It will also be understood by those of skill in the art that the terms proximal and distal, as used herein, describe a direction toward (proximal) and away from (distal) a surgeon or other user of the system.

Figure 1:
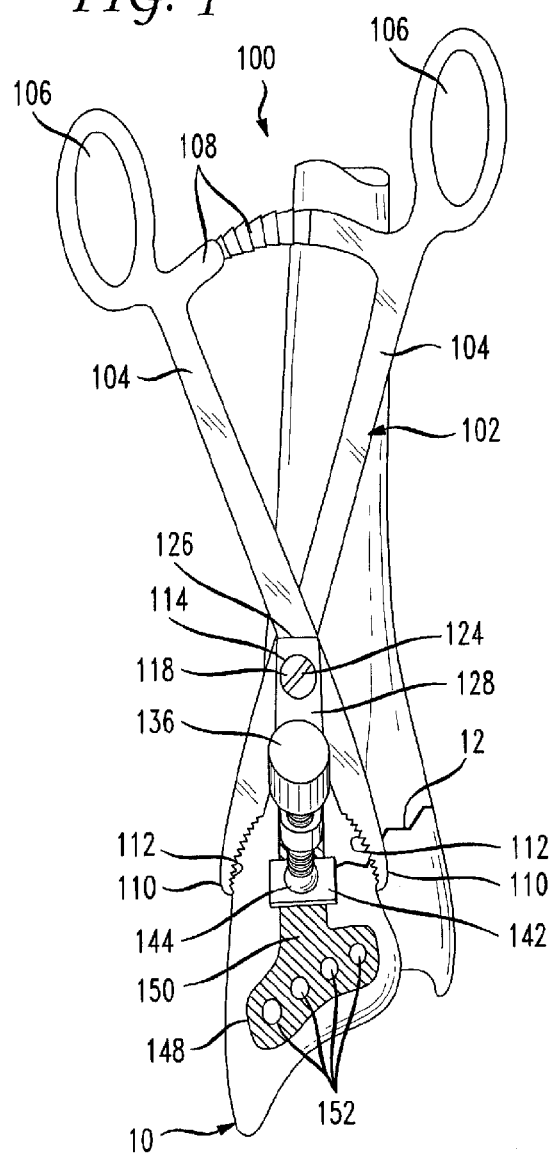
FIG. 1 shows a first perspective view of a bone fixation device according to the present invention.
Figure 2:
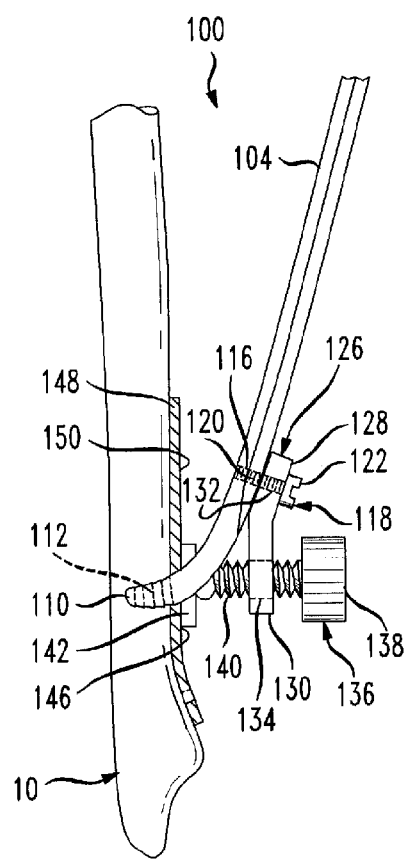
FIG. 2 shows a side view of the bone fixation device of FIG. 1.

As shown in FIGS. 1-2, a system 100 according to the present invention comprises a bone forceps 102 including two elongates arms 104. A first end of the bone forceps 102 comprises finger loops 106 to aid in the gripping and manipulation of the arms 104. The finger loops 106 also comprise corresponding arcs of interlocking teeth 108 configured to lockingly engage one another when pushed over one another, as those skilled in the art will understand, so that the position of the arms 104 relative to one another may be locked until manually disengaged. That is, as the arms 104 are rotated toward one another, the teeth 108 ratchet over one another preventing the arms 104 from being spread apart while permitting the arms 104 to be pushed further toward one another. The arms 104 extend to second ends 110 comprising gripping surfaces 112 adapted to frictionally grip items therebetween, as those skilled in the art will understand. The arms 104 also are pivotally coupled to one another at a joint 114 proximal of the second ends 110 by a predetermined distance. The joint 114 includes a bore 116 extending through each of the arms 104 with a clamping screw 118 pivotally received therein. For example, the clamping screw 118 may be formed with an elongated threaded shaft 120 and an increased diameter head 122 at a first end thereof. The head 122 further comprises a recess 124 configured to permit engagement with a tip of a driving mechanism, as those skilled in the art will understand. A second end of the shaft 120 may optionally comprise an increased diameter portion or other structure configured to prevent the screw 118 from being removed form the bore 116. Thus, the arms 104 define a substantially X-shaped instrument with the arcs of teeth 108 at the proximal end thereof and the gripping surfaces 112 at a distal end thereof. Portions of the arms 104 proximal of the joint 114 extend in a first plane while the portions thereof distal to the joint 114 including the gripping surfaces 112 bend away from this plane so that a target portion of bone may be gripped thereby while the proximal portions of the arms 104 extend away from the fracture site 12 (e.g., along a longitudinal axis of the bone 10).

As shown in greater detail in the side view of FIG. 2, the clamping screw 118 also secures an extension member 126 to the arms 104. Specifically, the exemplary extension member 126 is an elongated element extending having a proximal end coupled to the arms 104 and including a first section 128 extending from the proximal end substantially parallel to the portions of the arms 104 proximal of the joint 114 to a second section 130 extending away from the first section 128 at an angle selected so that, when the arms 104 are in a desired position gripping a fractured portion of bone 10, the second section 130 extends approximately parallel to a surface of the bone 10, as shown in the side view of FIG. 2.

A first bore 132 extending through the first section 128 is sized to receive the threaded shaft 120 of the clamping screw 118 therethrough while preventing the head 122 from being inserted therethrough. The second section 130 includes a second bore 134 extending therethrough configured to receive a set screw 136 having an increased diameter head 138 and a threaded shaft 140. A distal end of the threaded shaft 140 is connected to a plate shoe 142 via a ball joint 144 which facilitates the clamping of the bone plate 148 against the bone 10 even where the bone plate 148 is non-parallel to the section 130. For example, the ball joint may move through a range of motion of 0 to 30°. As will be described in more detail below, when the set screw 136 is tightened, the plate shoe 142 is urged against the bone plate 148 with the ball joint 144 permitting rotation of the plate shoe 142 until it is substantially parallel to the proximal surface of the bone plate 148. The plate shoe 142 has a distal face 146 configured to rest against a proximal face 150 of the bone plate 148 in an operative configuration. For example, where a proximal face 150 of the bone plate 148 is substantially planar, the distal face 146 of the plate shoe 142 will be substantially planar. The distal face 146 may include one or more spikes to dig into bone to enhance the grip against the bone. As the clamping screw 118 is tightened into the nut 126, the second section 130 of the nut 126 is moved closer to the bone 10 moving the set screw 136 and the plate shoe 142 closer to the bone plate 148, pressing the bone plate 148 against the bone 10.

In accordance with an exemplary method of the present invention, the bone forceps 102 are positioned over a fracture site 12 in the bone 10 so that the ridged surfaces 112 engage lateral portions of the bone 10. The interlocking teeth 108 may then be positioned over one another to lock the bone forceps 102 on the bone 10 in the desired position. The bone plate 148 is then placed over the fracture site 12 in a target orientation between the arms 104 of the bone forceps 102. In an initial configuration, the clamping screw 118 is loosely held within the first bore 132 so that the plate shoe 142 is separated from the bone 10 by a distance sufficient to permit the sliding of the bone plate 148 between the plate shoe 142 and the bone 10, as shown in FIG. 2. Once the bone plate 148 has been moved to a target orientation, the clamping screw 118 is tightened into the first bore 132 of the first section 128 pressing the plate shoe 142 against a proximal face 150 of the bone plate 148. Any known imaging technique may then be used to confirm that the bone plate 148 is in a desired orientation relative to the fracture site 12. If repositioning is required, the clamping screw 118 is loosened to ease the compressive force applied by the plate shoe 142 and the bone plate 148 is repositioned. The clamping screw 118 is again tightened and the process may then be repeated as many times as needed until the target orientation over the bone 10 has been reached harming the bone 10. Specifically, the exemplary embodiment of the present invention allows a physician or other user to reposition the bone plate 148 against the bone 10 as many times as needed without the risk of wearing away at the bone or otherwise causing trauma thereto. Once the target orientation has been reached, bone fixation devices (e.g., bone screws) may be inserted through any of the bone plate holes 152 to lock the position thereof prior to removal of the bone forceps 102 from the bone 10.

Although the present invention has been described with reference to preferred embodiments, it is submitted that various modifications can be made to the exemplary system and method without departing from the spirit and scope of the invention.

What is claimed is:

1. A device for the positioning of a bone plate against a target portion of bone, comprising:
   first and second arms pivotally connected to one another at a first joint, a distal end of each of the first and second arms defining a gripping surface configured to grip a target portion of bone therebetween, portions of the first and second arms proximal of the first joint extending substantially in a first plane;
   an extension member coupled to the first and second arms at the first joint, the extension member including a first section extending distally from the first joint substantially parallel to the first plane and a second section extending distally from the first section angled relative to the first section so that when the first and second arms are in a desired configuration gripping a target portion of bone, the second section extends substantially parallel to a surface of the target portion of bone;
   a compression mechanism coupled to the second section, the compression mechanism including a coupling member coupled between the second section of the extension member and a compression plate including a distal surface configured to engage a proximal surface of a bone plate to be coupled to the bone, the coupling member being movable relative to the second section of the extension member to move the compression plate toward and away from the second section.

2. The device of claim 1, wherein the compression plate is coupled to the coupling member via a second joint permitting angulation of the compression plate relative to the second section.

3. The device of claim 2, wherein the second joint is a ball joint.

4. The device of claim 1, wherein the coupling member is a set screw inserted through a threaded bore formed through the second section so that rotation of the set screw causes a corresponding movement of the compression plate relative to the second section.

5. The device of claim 3, wherein the ball joint allows the compression plate to rotate relative to the second section to adjust for an angulation relative to the second section of a bone plate received on the target portion of bone.

6. The device of claim 1, wherein the second section is angled so that, when the first and second arms are in the desired configuration gripping the target portion of bone, the second section extends substantially parallel to a longitudinal axis of the target portion of bone.

7. The device of claim 1, wherein a proximal end of each of the first and second arms comprises a gripping handle, and wherein a proximal portion of the first arm includes a first toothed arc extending toward a second toothed arc of the proximal portion of the second arm, the first and second toothed arcs being positioned so that, when the first and second arms are rotated about the joint toward one another, the first and second arcs overlie one another preventing the first and second arms from spreading apart from one another.

8. The device of claim 1, wherein the compression plate is moveable by the coupling member between a plate receiving position in which, when the first and second arms are in a desired configuration gripping a target portion of bone, the distal surface of the compression plate is spaced from a surface of the target portion of bone by a distance greater than a thickness of a bone plate to be coupled to the target portion of bone and a plate locking position in which the distal surface is moved toward a surface of the bone relative to the plate receiving position to clamp a plate received thereunder to the target portion of bone.

\* \* \* \* \*